US009138296B2

(12) United States Patent
Grabowski

(10) Patent No.: US 9,138,296 B2
(45) Date of Patent: Sep. 22, 2015

(54) PACKAGING FOR MEDICAL DEVICES WITH WINDOW

(71) Applicant: DEPUY SYNTHES PRODUCTS, LLC, West Chester, PA (US)

(72) Inventor: Woitech Grabowski, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 13/787,920

(22) Filed: Mar. 7, 2013

(65) Prior Publication Data

US 2013/0327667 A1 Dec. 12, 2013

Related U.S. Application Data

(60) Provisional application No. 61/656,229, filed on Jun. 6, 2012.

(51) Int. Cl.
A61B 17/06 (2006.01)
A61B 19/02 (2006.01)
B65B 5/04 (2006.01)
B65B 43/38 (2006.01)
B65D 5/42 (2006.01)
A61F 2/00 (2006.01)

(52) U.S. Cl.
CPC .............. A61B 19/026 (2013.01); A61F 2/0095 (2013.01); B65B 5/04 (2013.01); B65B 43/38 (2013.01); B65D 5/4204 (2013.01); A61B 2019/0201 (2013.01); A61B 2019/0209 (2013.01); A61B 2019/0267 (2013.01); A61B 2019/0286 (2013.01); A61F 2250/0091 (2013.01)

(58) Field of Classification Search
CPC ..... B65D 5/4204; A61B 19/02; A61B 19/026
USPC ......... 206/776, 777, 778, 438, 570, 571, 523, 206/583, 590; 229/162.1
See application file for complete search history.

(56) References Cited

U.S. PATENT DOCUMENTS 1,945,792 A * 2/1934 Stephens ....................... 206/769
1,968,943 A * 8/1934 Hermani ....................... 220/269
2,297,987 A * 10/1942 Ryerson ....................... 229/156
(Continued)

FOREIGN PATENT DOCUMENTS

EP 0 602 965 6/1994

Primary Examiner — Anthony Stashick
Assistant Examiner — James Way
(74) Attorney, Agent, or Firm — Fay Kaplun & Marcin, LLP

(57) ABSTRACT

An housing for a medical device includes an insert configured for removable insertion into the housing, outer dimensions of the insert conforming to inner dimensions of the housing to prevent movement thereof within the housing. The insert includes first and second planar walls connected to one another and having first and second openings extending therethrough. The first and second walls are movable between an open configuration in which the first and second walls are separated from one another and a closed configuration in which the first and second walls are folded to contact one another such that the first and second openings are aligned to define a medical device receiving cavity configured to house a medical device. In the closed configuration, the first and second walls apply a frictional clamping force to a packet containing the medical device to prevent movement of the medical device relative to the inlay.

20 Claims, 12 Drawing Sheets

(56) References Cited

U.S. PATENT DOCUMENTS

| | | | |
|---|---|---|---|
| 3,587,837 A * | 6/1971 | Smith et al. | 206/387.11 |
| 5,012,929 A * | 5/1991 | Roosa | 229/120.011 |
| 5,447,230 A * | 9/1995 | Gerondale | 206/363 |
| 6,006,917 A * | 12/1999 | Loeffler | 206/583 |
| 6,026,959 A * | 2/2000 | Lowe | 206/571 |
| 7,086,534 B2 * | 8/2006 | Roesel et al. | 206/583 |
| 7,128,208 B2 * | 10/2006 | Hull | 206/363 |
| 7,775,367 B2 * | 8/2010 | McDonald et al. | 206/583 |
| 7,780,004 B2 * | 8/2010 | Carlozzi et al. | 206/443 |
| 2005/0211595 A1 | 9/2005 | Hull | |
| 2012/0000905 A1 | 1/2012 | Noyelle et al. | |

* cited by examiner

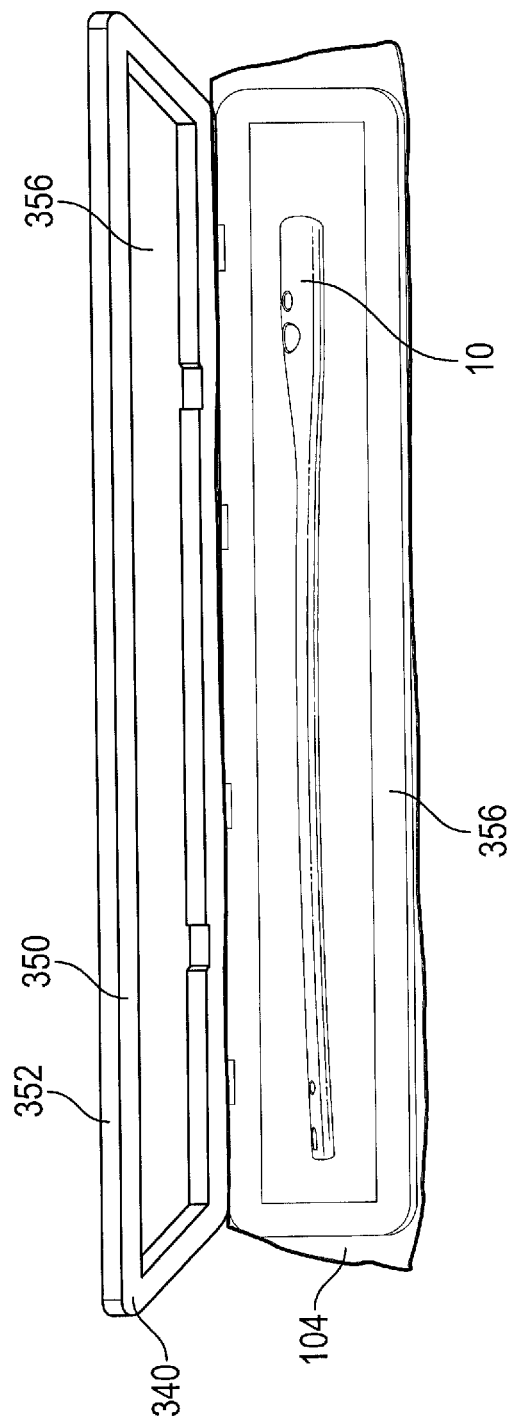
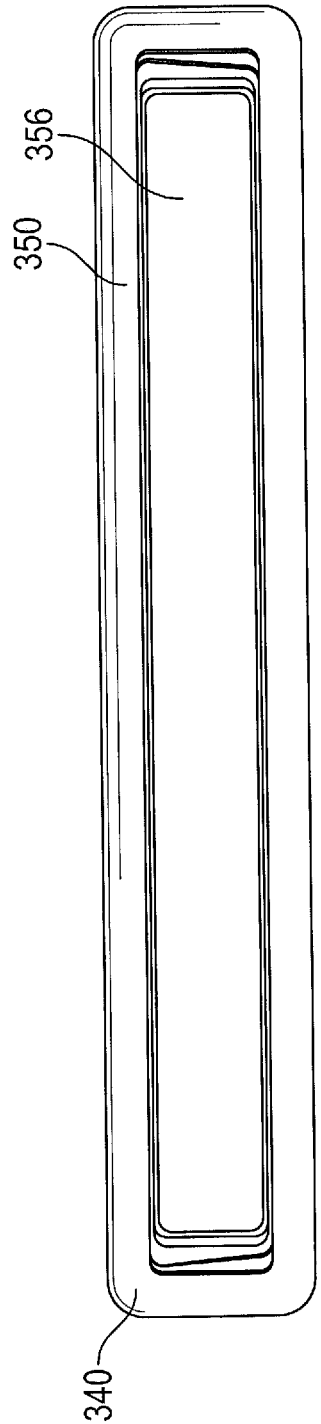
FIG. 9
FIG. 10

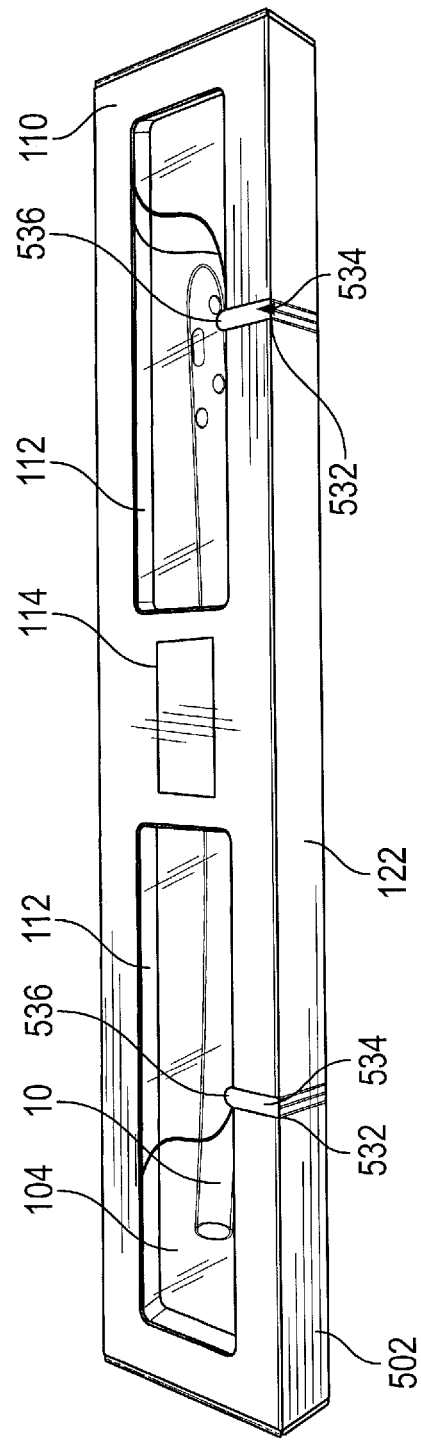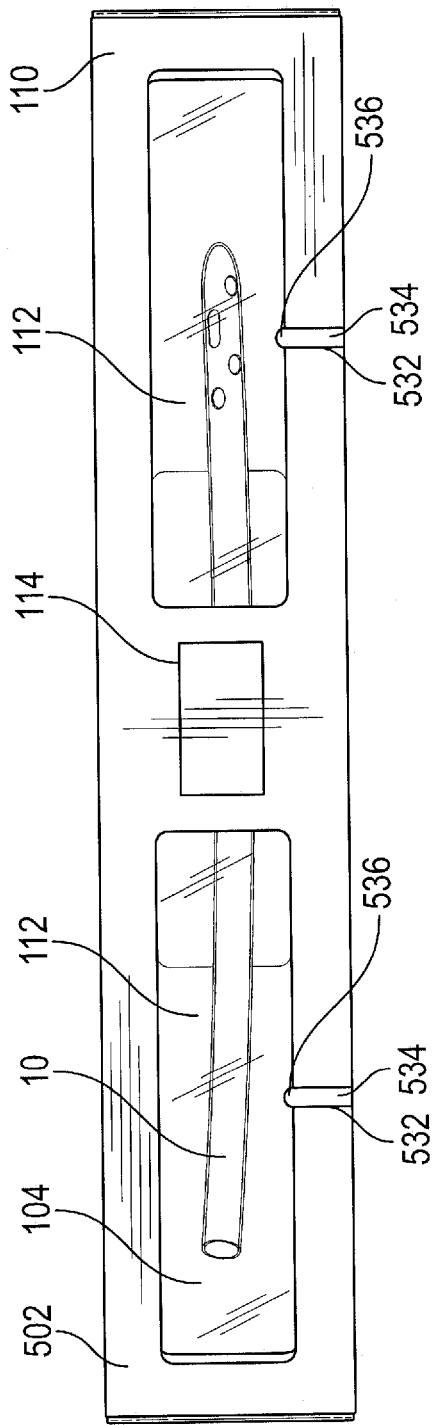
FIG. 16
FIG. 17

PACKAGING FOR MEDICAL DEVICES WITH WINDOW

PRIORITY CLAIM

The present application claims priority to U.S. Provisional Appln. Ser. No. 61/656,229 entitled "Packaging for Medical Devices with Window" filed on Jun. 6, 2012, the entire disclosure of which is incorporated herein by reference.

BACKGROUND INFORMATION

Medical devices must be packaged and sealed such that the devices remain sterile until ready for use. Furthermore, the packaging must be configured to prevent damage to the device during transport. Thus, current packages for medical devices are generally include excess padding and are often configured such that the device is not visible until the packaging has been removed. Thus, it is often not possible to determine the type of medical device contained within a package without compromising the sterility of the device.

SUMMARY OF THE INVENTION

The present invention is directed to a housing for a medical device, comprising an insert configured for removable insertion into the housing, outer dimensions of the insert conforming to inner dimensions of the housing to prevent movement of the insert within the housing. The insert comprises first and second planar walls connected to one another and having first and second openings extending therethrough, respectively, the first and second walls being movable between an open configuration in which the first and second walls are separated from one another and a closed configuration in which the first and second walls are folded to contact one another along a length thereof such that the first and second openings are aligned with one another to define a medical device receiving cavity configured to house a medical device, wherein, in the closed configuration, the first and second walls apply a frictional clamping force to a packet containing the medical device to prevent movement of the medical device relative to the inlay.

BRIEF DESCRIPTION OF THE DRAWINGS

FIG. 9 shows a perspective view of the packaging insert of FIG. 8 in a partially folded configuration;

FIG. 10 shows a perspective view of the packaging insert of FIG. 8 in a fully folded configuration;

FIG. 16 shows a first perspective view of a packaging according to a third embodiment of the invention in an operative configuration with the packaging insert of FIG. 13;

FIG. 17 shows a second perspective view of the packaging of FIG. 16;

DETAILED DESCRIPTION

Figure 1:
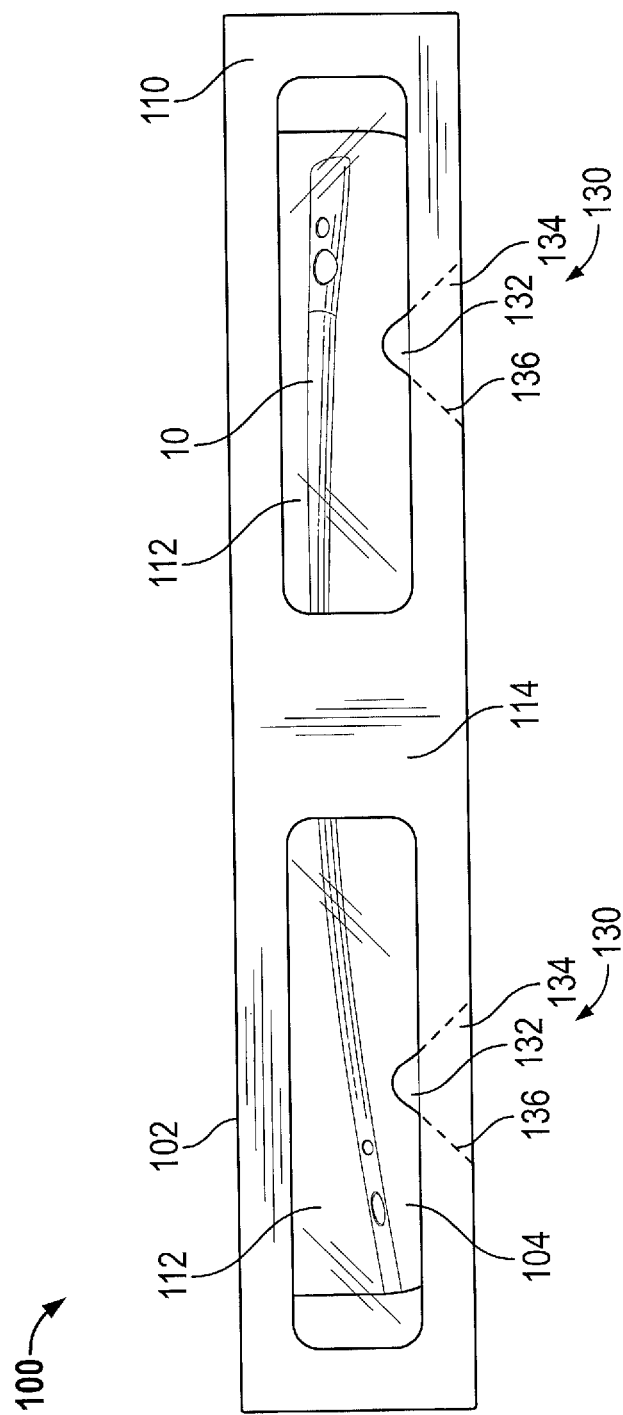
FIG. 1 shows a first perspective view of an exemplary packaging according to a first embodiment of the invention.

The present invention may be further understood with reference to the following description and the appended drawings, wherein like elements are referred to with the same reference numerals. The present invention relates to packaging and, in particular, relates to packaging for medical devices. An exemplary embodiment of the present invention is directed to a box configured to house a medical device sealed within a packet and including one or more windows positioned to permit visualization of the device without having to open the box or remove the packaging. The exemplary packaging according to the invention comprises an insert positioned within the box and configured to frictionally clamp the medical device therein. The insert may be one of removably insertable into the packaging or integrally formed therewith. In one embodiment, the insert may be removably insertable into the box and may include first and second walls connected to one another with first and second openings extending through the first wall and second wall, respectively. The first and second walls are movable between an open configuration in which the first and second walls are separated from one another and a closed configuration in which the first and second walls are folded to contact one another along a length thereof such that the first and second openings are aligned to define a medical device receiving cavity. In an operative configuration, a packet (e.g., a sterile plastic casing) housing the medical device is clamped between the first and second walls with the medical device seated in the cavity. The frictional pressure applied by the first and second walls of the insert to the packet prevents movement of the packet and medical device relative to the insert. The insert is formed with dimensions substantially equivalent to dimensioned of an interior space of the box so that the insert is immovable when housed within the box. Thus, the frictional pressure applied to the packet by the insert prevents damage to the medical device during transport while also keeping the medical device aligned with windows provided on the box to permit visualization thereof. The exemplary packaging system according to the invention significantly reduces or eliminates the need for foam padding as currently used in transporting medical devices, thus reducing waste. In another embodiment of the invention as will be described in greater detail later on, the insert may be integrally formed with the box and may be used in conjunction with a foam or cardboard insert. The exemplary box according to the invention may be one or both of top-loading or side-loading, as will be described in greater detail later on, to permit access to the medical device in a desired manner.

Figure 2:
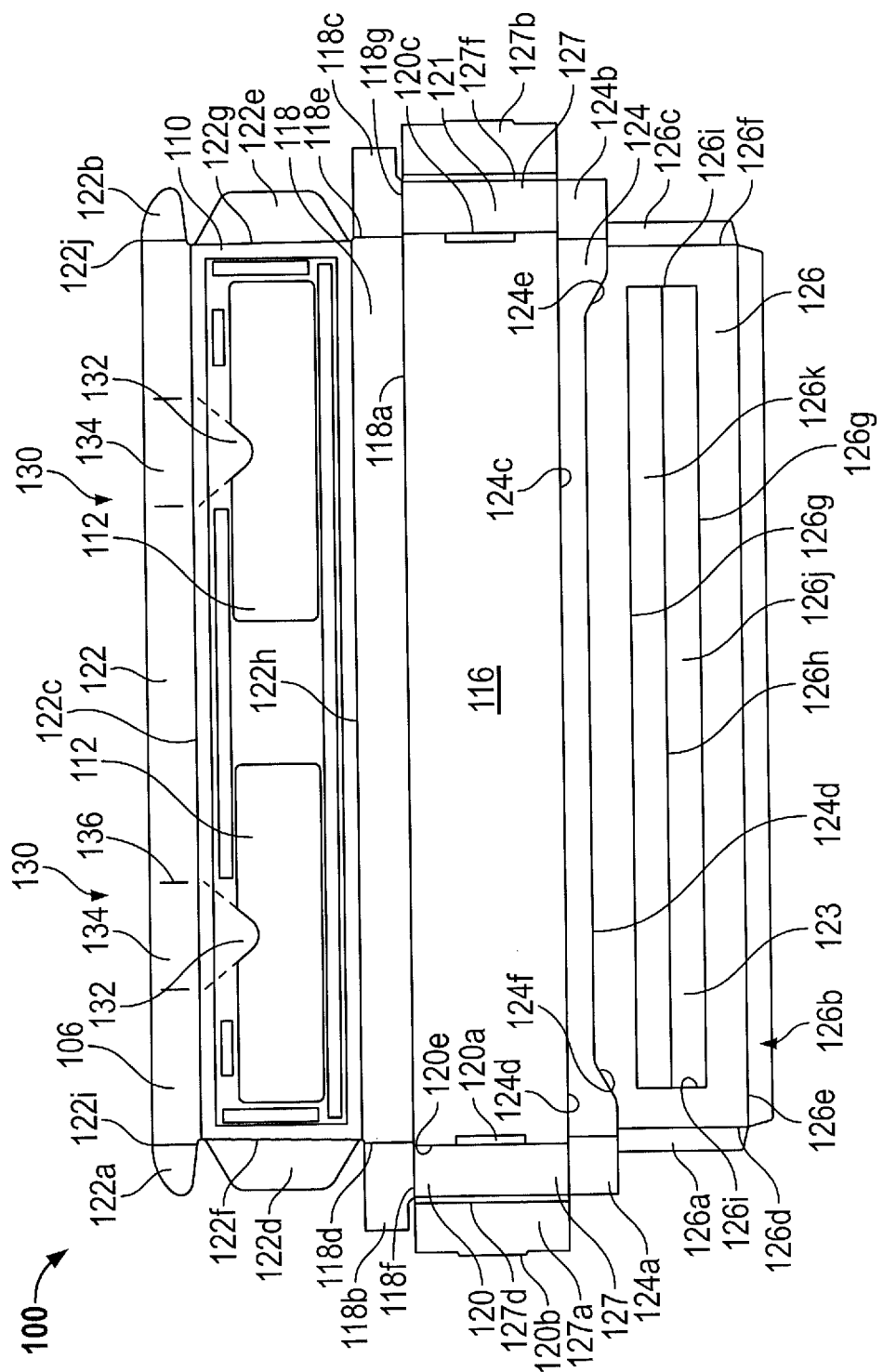
FIG. 2 shows a second perspective view of the packaging of FIG. 1 in a non-assembled configuration.

As shown in FIGS. 1-4, a package 100 according to an exemplary embodiment of the present invention comprises a box 102 sized and shaped to house a medical device 10 (e.g., a bone plate, intramedullary rod, bone screw, or any other bone fixation element) sealed in a packet 104 such that the device remains sterile prior to use. The packet 104 is preferably formed of a transparent material such that the device sealed therewithin is visible through the packet 104. The packet 104 may be, for example, a substantially flat, sealed pouch entirely housed within the box 102, as will be described in greater detail later on. The box 102 may be substantially rectangular in shape with dimensions selected to house the medical device 10 while preventing damage thereof during transport. It is noted, however, that the box may be formed in any other shape without deviating from the scope of the invention and to conform to the shape and size of one or more medical devices housed therein. In an exemplary embodiment, the box 102 is formed from a single piece 106 of cardboard, as shown in FIG. 2. Specifically, the shape of the cardboard may be cut (i.e., via die-cutting) and provided with a plurality of fold lines permitting folding thereof into the desired shape, as those skilled in the art will understand. As understood by those of skill in the art, an outer surface of the box 102 is formed of six planar surfaces. A top surface 110 of the box 102 comprises two windows 112 configured to permit visualization of the interior space of the box. Each of the windows 112 may include a transparent film extending there across to cover the window 112 while also permitting the contents of the box 102 and/or the packet 104 to be visible therethrough. The windows 112 may, for example, be substantially rectangular with rounded corners although any other shape is envisioned without deviating from the scope of the invention including, but not limited to, square, oval and circular. The top surface 110 may also have labeling 114 having one or more of an image, name and specifications of the medical device 10 housed therewithin. In another embodiment of the invention, windows 112 may be provided on any other outer surface of the box in any size and arrangement. In one embodiment, the box 102 may comprise only one window 112 extending across the top surface 112 such that the entire length of a bone fixation device housed therewithin. In this embodiment, the labeling 114 may extend over a periphery of the window 112 on the top surface 110. In yet another embodiment, the labeling 114 may be provided on any other surface of the box (e.g., the bottom surface 116).

In another embodiment, the windows 112 may be arranged substantially as shown on the top surface 110 and an additional window may be provided on the bottom surface 116, as described in greater detail with respect to FIGS. 16-19. Specifically, the windows 112 on the top surface 110 may be positioned substantially adjacent to the first and second side surfaces 120, 121 while the window on the bottom surface 116 may be substantially centrally located. This arrangement permits that substantially the entire medical device 10 may be visible through the combination of the windows on the top and bottom surfaces 110, 116.

As shown in FIG. 2, the sheet 106 also defines a bottom surface 116, back surface 118, first and second side surfaces 120, 121, a first front surface 122 and a second front surface 124. The second front surface 124 is further connected to an inlay surface 126 which may be folded into a cavity of the box 102 in an operative configuration, as will be described in greater detail hereinafter. The inlay surface 126 may include a seating portion 123 configured and dimensioned to permit seating of the medical device 10 thereon. The seating portion 123 is defined by a pair of fold lines 126g and slits 126h, 126i which form seating flaps 126j, 126k. In an operative configuration, the seating flaps 126j, 126k may be folded down at the lines 126g to define a cavity over which the medical device 10 may be seated. It is noted that each of the surfaces described hereinafter are bordered by fold lines which may be score lines defining a line about which the surfaces may be folded relative to one another. In an operative configuration, the first front surface 122 and the back surface 118 are folded about a line 118a. Tabs 118b, 118c formed on lateral sides of the back surface 118a are then folded about their respective lines 118d, 118e to align bottom edges 118f, 118g of the tabs 118b, 118c with lines 120c, 120e, respectively. The second front surface 124 is then folded about a line 124c to bring the inlay surface 126 substantially over the bottom surface 116. Tabs 124a, 124b are then folded to align the bottom edges 124d, 124e, 124f with the lines 120c, 120e, respectively. The inlay surface 126 is connected to the second front surface 124 only at the line 124d, the edges 124e, 124f being cut separate from the inlay surface 126 to permit a folding thereof, as will be described in greater detail later on.

Figure 3:
FIG. 3 shows a first perspective view of a packaging of FIG. 1 in an assembled configuration.

Side walls of the box 102 including the first and second side surfaces 120, 121 are formed by folding flaps 127 about the lines 120c, 120e and subsequently folding flaps 127a, 127b about respective fold lines 120d, 120f. A protruding portion 120b of each flap 127 is then secured within a slot 120a formed through the bottom surface 116. This folding step also seats the tabs 118b, 118c and tabs 124a, 124b between the inlay surface and the first and second side surfaces 120, 121. The inlay 129 is then formed by folding tabs 126a, 126b, 126c about their respective fold lines 126d, 126e, 126f. In this configuration, the inlay surface 126 is folded about line 124d and the tabs 126a, 126b, 126c are seated against the first side surface 120, the back surface 118 and the second side surface 121, respectively such that the inlay surface 126 is separated from the bottom surface 116 and fully supported by the tabs 126a, 126b, 126c. This partially assembled configuration is depicted in FIGS. 3 and 4.

Figure 4:
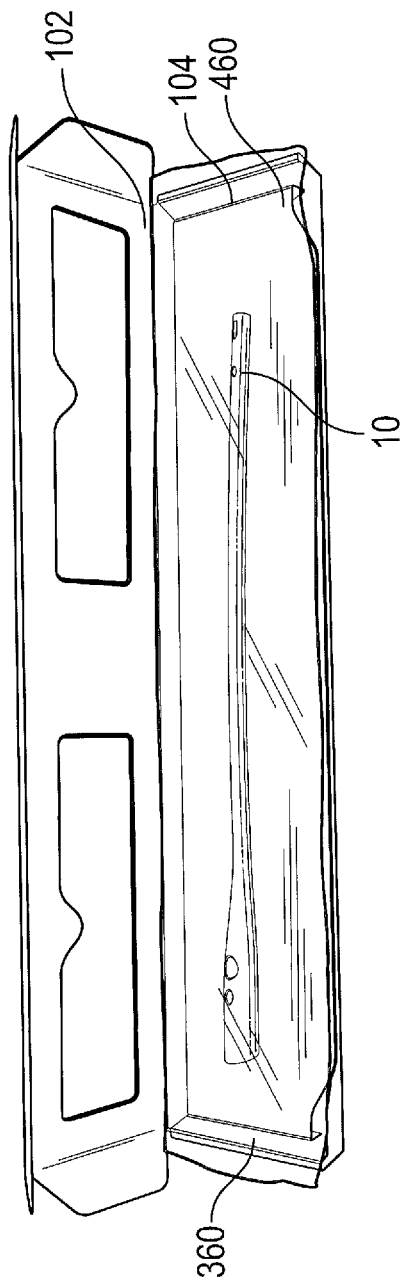
FIG. 4 shows a second perspective view of a packaging of FIG. 1 in an assembled configuration housing a medical device therein.

In an operative configuration, the medical device 10 may be positioned over the inlay 129, as shown in FIG. 4 and an inlay 140, 240 may be positioned over the inlay 129, as will be described in greater detail below. The box 102 is then closed by folding tabs 122d, 122e about their respective lines 122f, 122g and then folding the first front surface 122 about line 122h. The tabs 122d, 122e are then inserted into slots 133a, 133b formed by insertion of the tabs 126a, 126b adjacent the first and second side surfaces 120, 121. The first front surface 122 is then further folded along line 122c. Wings 122a, 122b are then folded about their respective lines 122i, 122j and inserted into respective slots 133c, 133d formed by the folding and capturing of tabs 124a, 124b by the flaps 127a, 127b. In an exemplary embodiment, insertion of the wings 122a, 122b into the slots 133c, 133d is sufficient to maintain the box 102 in the closed configuration. In an alternate embodiment, an adhesive may be use to further maintain the box 102 in the closed configuration.

In one exemplary embodiment, the box 102 may further comprise two sealing arrangements 130. It is noted however that any number of sealing arrangements 130 may be used without deviating from the scope of the invention. The sealing arrangement 130 is formed as a pull tab 132 connected to a perforated portion 134 defined by perforations 136 on lateral sides thereof. As shown in FIGS. 1 and 2, the perforated portion 134 extends from the tab 132 on the top surface 110 to an edge of the first front surface 122. In an operative configuration, a user may grip and pull back on each of the tabs 132 to tear the perforated portion 134 away from the box 102, permitting the top surface 110 to be folded back and providing access to the interior space of the box 102. The tab 132 may also include printed text which identifies a direction in which the tab 132 is to be pulled. In addition to being easy to use, the tear-off sealing arrangement 130 is tamper-evident, thus ensuring the sterility of the medical device 10.

In another embodiment of the invention (not shown), the box 102 may include a perforated slit extending along line 122c and omit the sealing arrangements 130. In this embodiment, the box 102 may be opened by tearing the perforated slit along the line 122c to lift the top surface 110 away from the box 102 and provide access to the medical device 10 contained therein.

Figure 5:
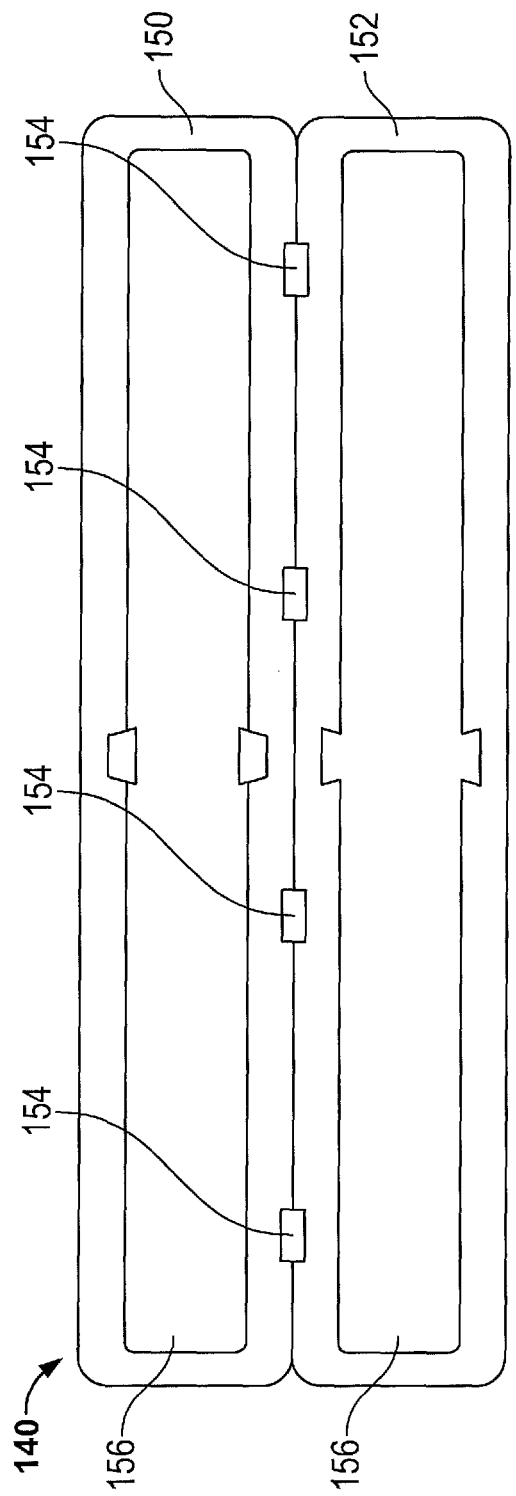
FIG. 5 shows a perspective view of a packaging insert according to a first exemplary embodiment of the invention.

In one embodiment of the invention, the box 102 further comprises an inlay 140 removably housed in the interior space and configured to provide padding to the medical device 10, as shown in FIG. 5. The inlay 140 may be formed of one of cardboard, foam and another suitable material known to those of skill in the art. The inlay 140 comprises first and second walls 150,152 connected to one another about one or more hinge points 154. The first and second walls 150, 152 may be movable from a closed configuration in which the first and second walls 150, 152 are in contact with one another and an open configuration in which the first and second walls 150, 152 are separated from one another about the hinge points 154. Each of the first and second walls 150, 152 comprises an opening 156 configured and dimensioned to house the medical device 10 therein. The openings 156 may be aligned with the windows 112 of the box 102 so that when the inlay 140 is seated within the cavity of the box 102, the medical device 10 positioned in the openings 156 is visible. In an exemplary embodiment, a combined thickness of the first and second walls 150, 152 may be substantially equivalent to a remaining thickness of the box 102 once the inlay 129 has been folded into the configuration described above to prevent and/or inhibit movement of the inlay 140 therewithin. Although the inlay 140 is depicted with substantially rectangular openings 156 having rounded corners, it is noted that any other shape of the openings 156 is envisioned without deviating from the scope of the invention.

In an operative configuration, the box 102 may be assembled as disclosed above. The packet 104 containing the medical device 10 may then be positioned over the seating portion 123 of the inlay 129, as shown in FIG. 4. The inlay 140 may then be moved to the closed configuration and placed over the packet 104. The inlay 140 is configured such that, when inserted over the packet 104, the packet 104 is prevented from moving within the box 102. By preserving the integrity of the packet 104, the inlay 140 according to the invention ensures that the contents thereof, namely the medical device 10, remain both sterilized and undamaged.

Figure 6:
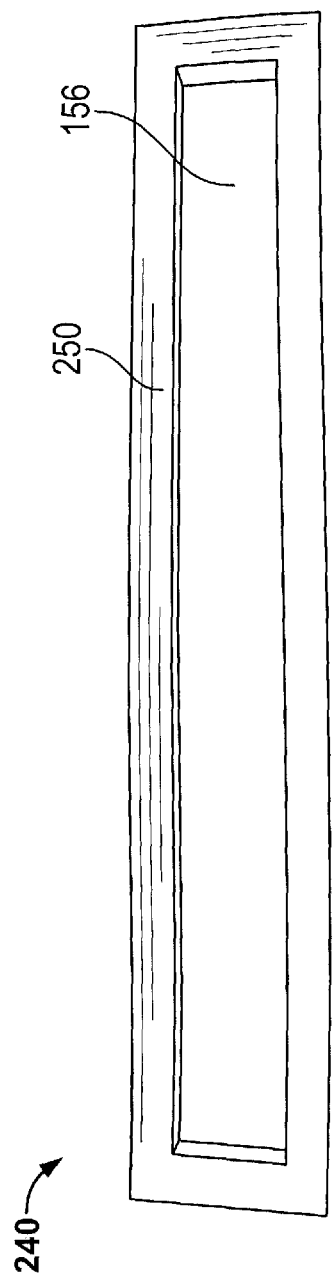
FIG. 6 shows a perspective view of a packaging insert according to a second exemplary embodiment of the invention.
Figure 7:
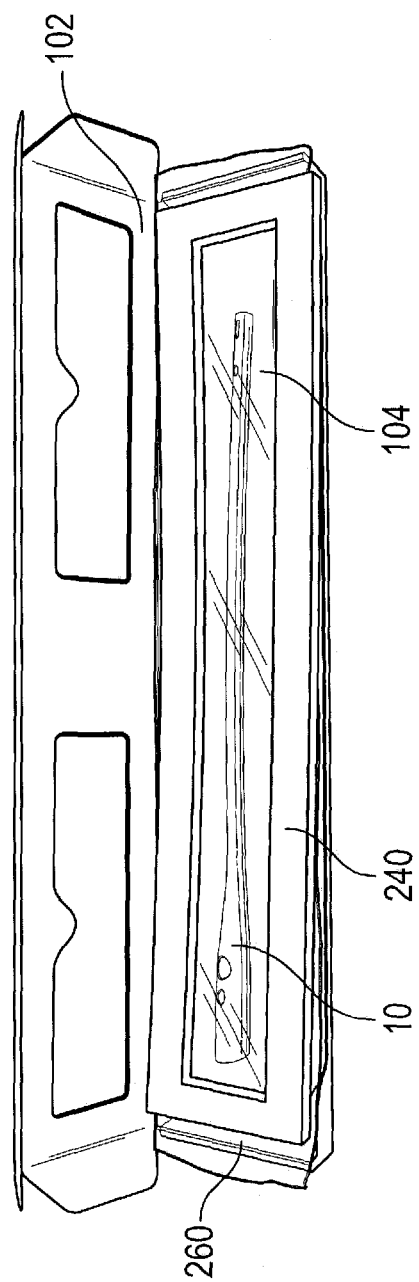
FIG. 7 shows a perspective view of the packaging of FIG. 6 seated within the packaging of FIG. 1.

FIGS. 6-7 depicts an inlay 240 according to another embodiment of the invention, the inlay 240 configured for use with the box 102. The inlay 240 is formed substantially similar to the inlay 140 but is formed of a foam material. However, whereas the inlay 140 includes first and second walls 150, 152 connected to one another at hinge points 154, the inlay 240 is formed with a single wall 250 dimensioned to be positioned over the medical device 10 and inlay 129 of the box 102 in an operative configuration. Specifically, as described in greater detail earlier, the wall 250 is dimensioned such that when the packet 104 is inserted over the inlay 129, the medical device 10 is prevented from movement within the box 102. The packet 104 may be dimensioned such that a longitudinal length of the packet 104 is greater than a longitudinal length of the inlay 129 and the box 102, producing an overhang 260 of the packet 104 on one or both ends of the box 102. The inlay 240 is then positioned over the inlay 129 and the packet 104. The one or both overhangs 260 of the packet 104 may then be folded over the respective ends of the inlay 240. The box 102 may then be closed in accordance with the method disclosed earlier. As those skilled in the art will understand, the exemplary foam material according to this embodiment has a density selected to provide a sufficient frictional pressure to the packet 104 while also providing improved impact absorption, thereby reducing damage to the medical device 10 during transport. As those skilled in the art will understand, the impact absorption of the foam inlay 240 is particularly advantageous in transportation of medical devices 10 (e.g., for sales demonstrations, etc.).

Figure 8:
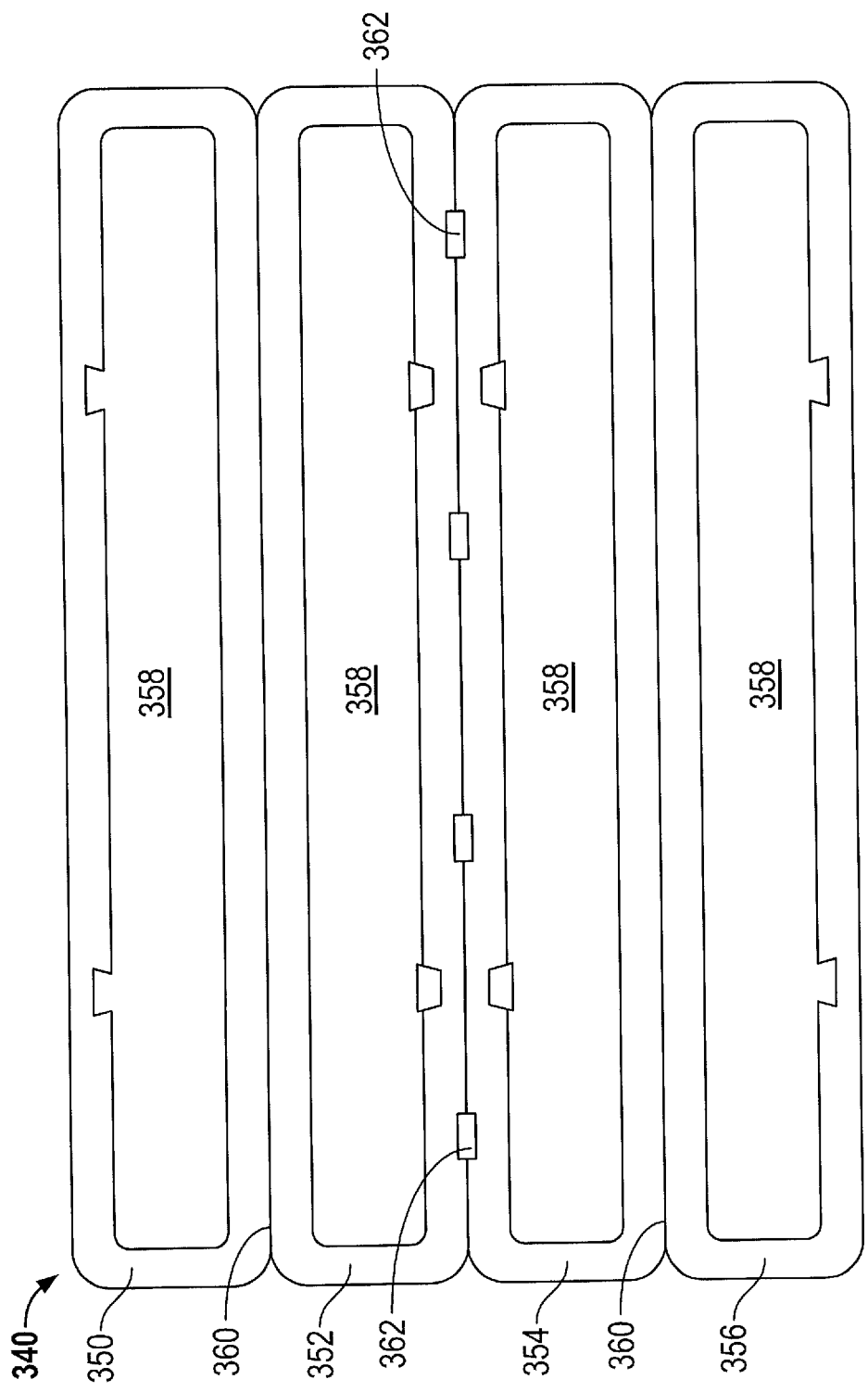
FIG. 8 shows a perspective view of a packaging insert according to a third exemplary embodiment of the invention in an open configuration.

FIGS. 8-10 describe an inlay 340 according to another alternate embodiment of the invention. The inlay 340 may be formed substantially similarly to the inlay 140 and may comprises first, second, third and fourth walls 350, 352, 354, 356, each having an opening 358 formed substantially similarly to the openings 156 of FIG. 5. The first and second walls 350, 352 are formed from a single sheet of, for example, cardboard having a fold line 360. Similarly, the third and fourth walls 354, 356 are also formed from a single sheet of the cardboard having a fold line 360. In an operative configuration, the walls are folded about the fold line such that the openings 358 are aligned with one another. The second and third walls 354, 356 are hingedly connected to one another via one or more hinges 362 as described in greater detail with respect to FIG. 5. In operation, the first, second, third and fourth walls 350, 352, 354, 356 are folded such that all the openings 358 are in alignment with one another to define a medical device receiving cavity. Specifically, in a first operative configuration, the first wall 350 is folded over the second wall 352 and the fourth wall 356 is folded over the third wall 354, as shown in FIG. 9. The packet 104 containing the medical device 10 is inserted between the first and fourth walls 352, 356 and held therein via a frictional engagement. Each of the first, second, third and fourth walls 350, 352, 354, 356 may have the same width, a combined width of the first, second, third and fourth walls 350, 352, 354, 356 being substantially equivalent to a width of a box 202 with which the inlay 340 is to be used, as will be described in greater detail later on, to prevent movement of the inlay 340 within the box 202. In another embodiment, the first, second, third and fourth walls 350, 352, 354, 356 may be formed with varying thicknesses. As those skilled in the art will understand, the multiple layers of the exemplary inlay 340 of FIGS. 8-10 provides added structural integrity and padding to the medical device 10 housed therein.

Figure 11:
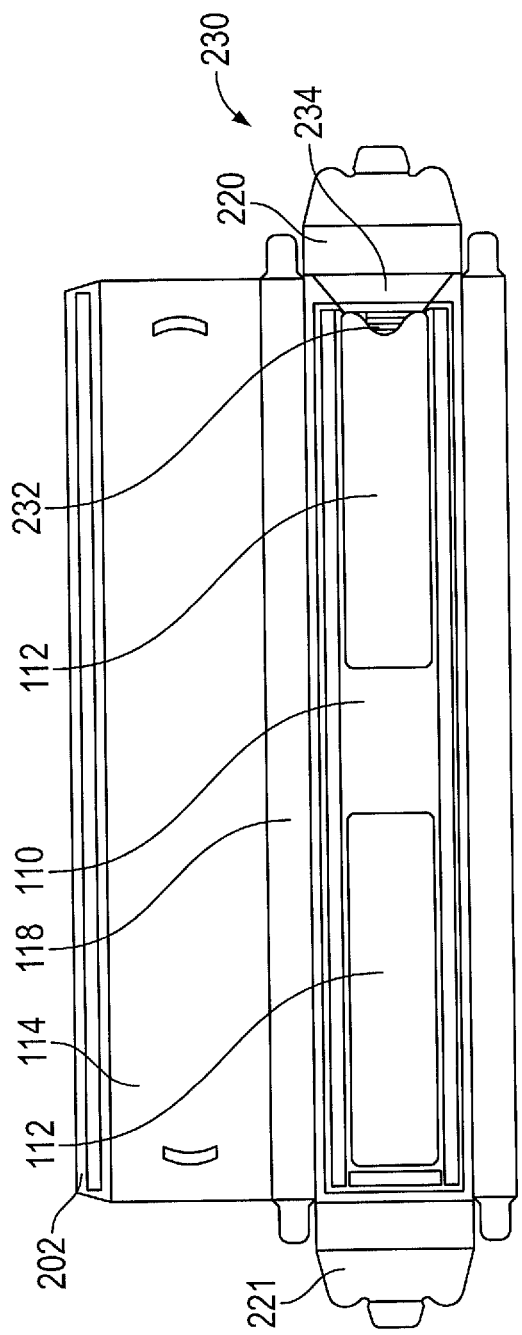
FIG. 11 shows a perspective view of a packaging according to a second embodiment of the invention in a non-assembled configuration.
Figure 12:
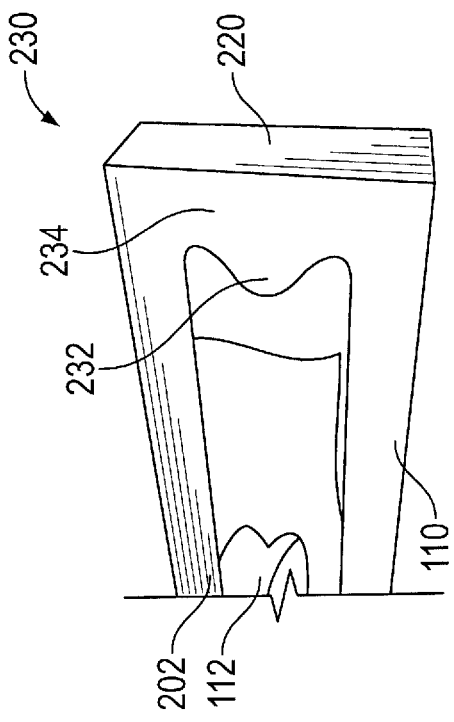
FIG. 12 shows a perspective view of the packaging of FIG. 12 in an assembled configuration.

FIGS. 11-12 depict the exemplary box 202 according to another embodiment of the invention, the box 202 being formed substantially similarly to the box 102, wherein like elements have been referenced with like reference numerals. However, whereas the box 102 includes an integrally formed inlay 129, the box 202 is configured for use with one or more removable inlays. Furthermore, whereas the box 102 is top-loading, the box 202 is side-loading. It is noted, however, that the box 202 may be constructed with a top-loading design without deviating from the scope of the invention. The box 202 comprises a sealing arrangement 230 having a tab 232 open to a perforated portion 234 extending from the top surface 110 to the first side surface 120 so that tearing of the perforated portion 234 permits a first side surface 220 to be folded away from the box 202. In operation, once a user has opened the sealing arrangement 230, the inlay 340 may be withdrawn from the side of the box 202 and subsequently opened to permit withdrawal of the packet 104 containing the medical device 10. It is noted that the sealing arrangement 230 may be positioned on either side surface of the box 202 without deviating from the scope of the invention. Furthermore, the box 202 may comprise sealing arrangements 230 adjacent both first and second side surfaces 220, 221 to permit a user to open the box from a desired side.

Figure 13:
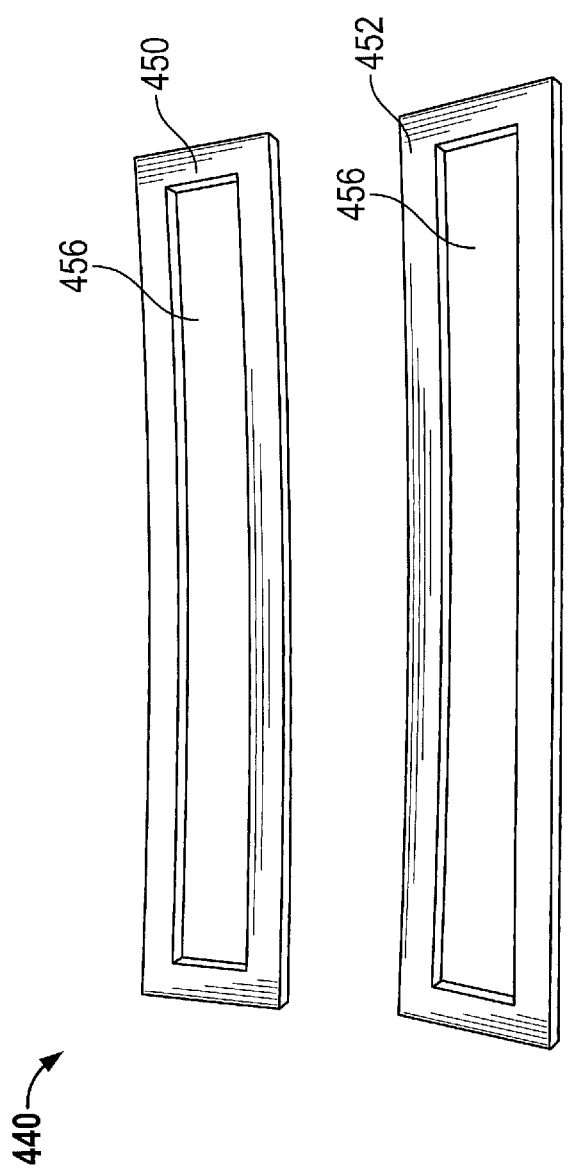
FIG. 13 shows a perspective view of a packaging insert according to a fourth exemplary embodiment of the invention.

FIG. 13 depicts an inlay 440 according to yet another embodiment of the invention, the inlay 440 being formed substantially similar to the inlay 140 of FIG. 5 and being employed with the box 202 in an operative configuration. However, whereas the inlay 140 includes first and second walls 150, 152 connected to one another at hinge points 154, first and second walls 450, 452 of the inlay 440 are formed separate from one another. The first and second walls 450, 452 may be dimensioned such that when the packet 104 is inserted therebetween, the medical device 10 is suspended between top and bottom surfaces of the box 202. In another embodiment, the medical device 10 may contact one or both of the top and bottom surfaces of the box 202 when housed therewithin. In an exemplary embodiment, both the first and second walls 450, 452 of the inlay 440 may be formed of a foam material. In an alternate embodiment, one or both of the first and second walls 450, 452 may be formed of cardboard.

Each of the first and second walls 450, 452 comprises an opening 456 configured and dimensioned to house the medical device 10 therein. The openings 456 may be substantially aligned with the windows 112 of the box 202 so that when the inlay 440 is seated within the cavity of the box 202 the medical device 10 is at least partially visible. The openings 456 may have a substantially rectangular shape with 90° corners. In another embodiment, the openings 456 may have substantially rounded corners similar to the openings 156.

Figure 14:
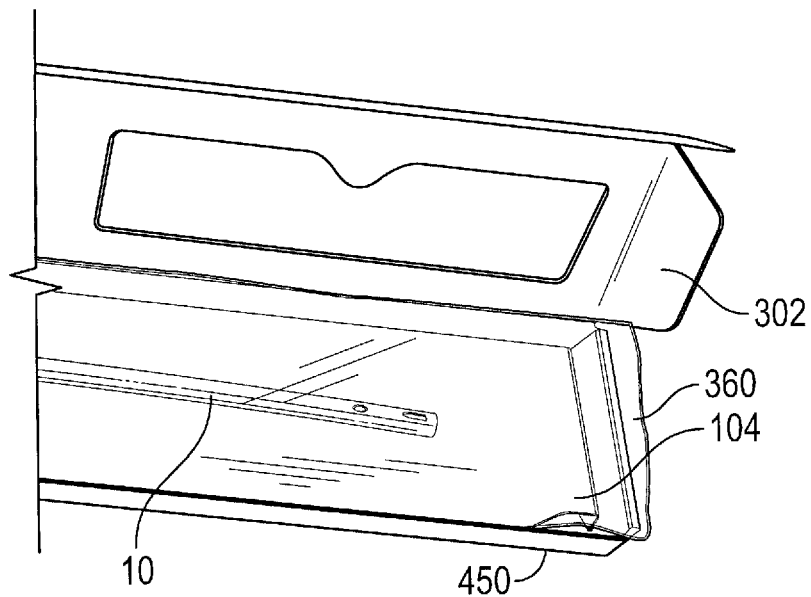
FIG. 14 shows a perspective view of the packaging of FIG. 13 in a first operative configuration within a box according to a third embodiment of the invention.
Figure 15:
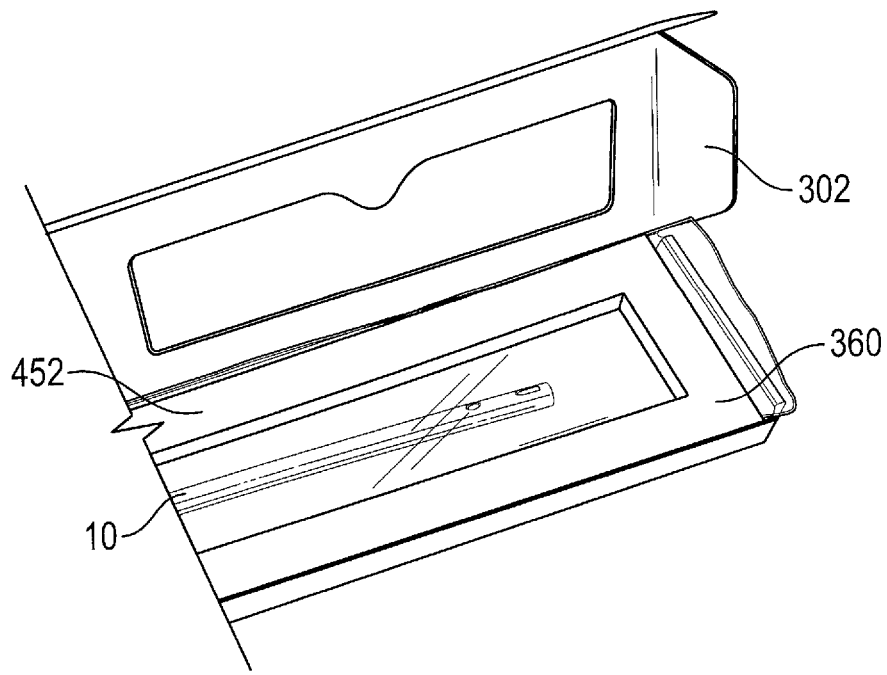
FIG. 15 shows a perspective view of the packaging insert of FIG. 13 in a second operative configuration within the box according to the third embodiment of the invention.
Figure 18:
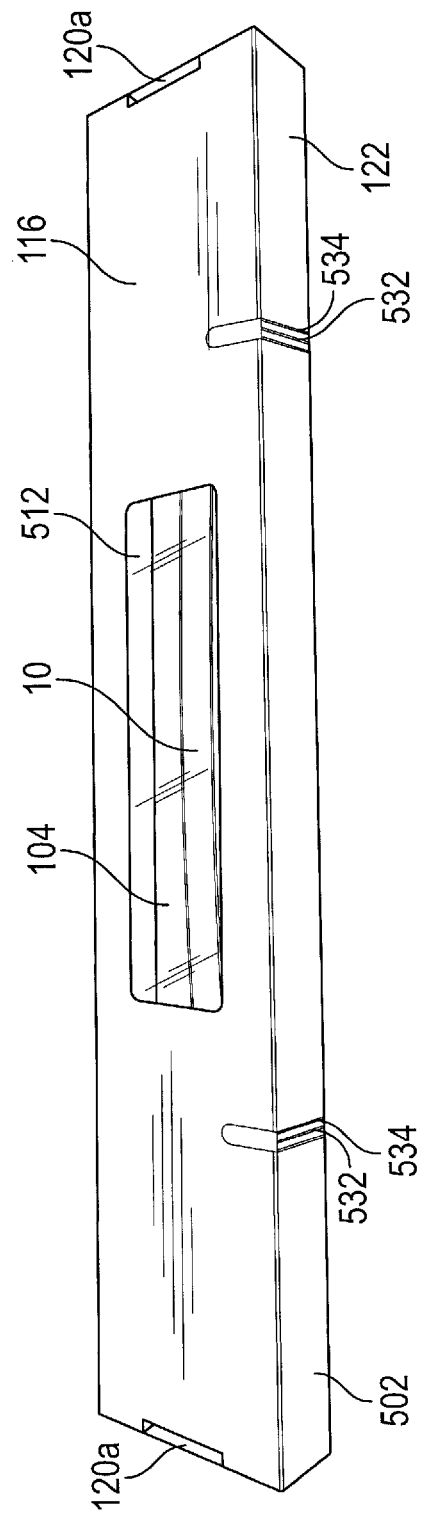
FIG. 18 shows a third perspective view of the packaging of FIG. 16.
Figure 19:
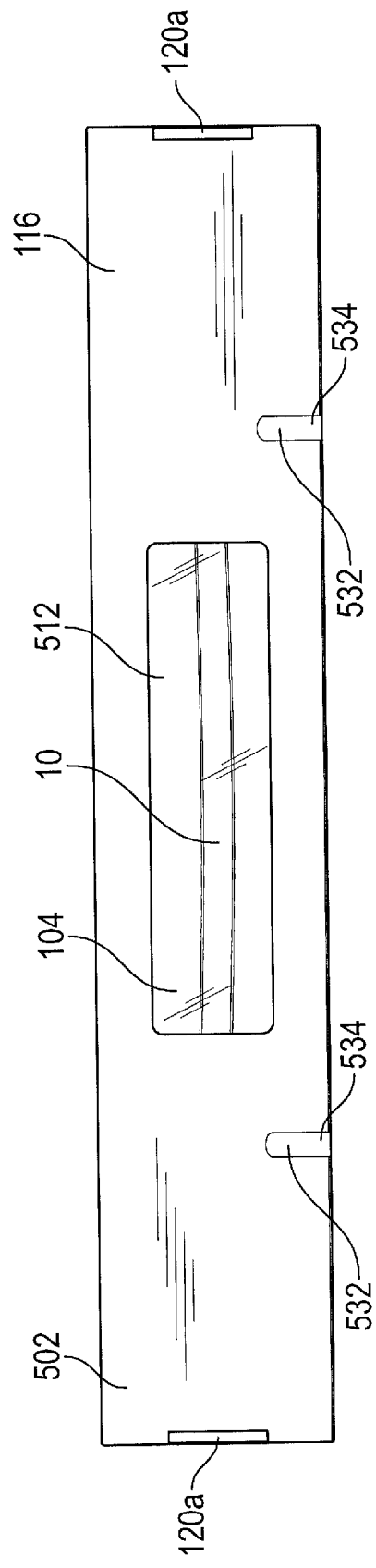
FIG. 19 shows a fourth perspective view of the packaging of FIG. 16.

FIGS. 14-15 depict the inlay 440 in an operative configuration with a box 302. The box 302 is formed substantially similar to the box 102 but does not include an integrally formed inlay 129. Rather, the inlay 129 is replaced by the use of first and second walls 450, 452. In an operative configuration, the first wall 450 is first positioned with the box 302. The packet 104 including the medical device 10 is then positioned over the first wall 450, a longitudinal length of the packet 104 being greater than a longitudinal length of the inlay 440 and the box 102, producing the overhang 260, as described in greater detail earlier. The second wall 452 is then positioned over the first wall 450 and the packet 104 such that the medical device 10 is seated within the openings 456. The one or both overhangs 260 of the packet 104 may then be folded over the respective ends of the second wall 452. The box 102 may then be closed. The exemplary foam material according to this embodiment has a density selected to provide a sufficient frictional pressure to the packet 104 while also providing improved impact absorption, thereby reducing damage to the medical device 10 during transport.

FIGS. 16-19 depict a box 502 according to another embodiment of the invention. The box 502 is formed substantially similarly to the box 102, wherein like element have been referenced with like reference numerals. Similarly to the box 102, the box 502 also includes two windows 112 on the top surface 110. Each of the windows 112 is attached to a sealing arrangement 530 which includes a removable label 532. The removable label 532 may have a first, sticky portion 534 at a junction of the top surface 110 and the first front surface 122 with the bottom surface 116 to maintain the box 102 in the closed configuration. A non-sticky portion 536 may extend away from the sticky portion 534 and may include written details of the contents of the box 102 or any other information pertaining to a use and/or handling of the box 502. To remove the removable label 532 from the box 502, an operator may grasp and pull the non-sticky portion 536 away from the box 502. In an exemplary embodiment, the sticky portion 534 may be removed from and re-attached to the box 502 a plurality of times without adversely affecting adhesive properties thereof, as those skilled in the art will understand. In an exemplary embodiment, the box 502 may include the removable labels 532 adjacent each of the windows 112. It is noted, however, that the box 502 may include any number of removable labels 532 without deviating from the scope of the invention.

In accordance with an exemplary embodiment of the invention, the construction of the box 502 may be substantially similar to the box 102. In an alternate embodiment however, the wings 122a, 122b may be omitted. The box 502 according to the invention also includes a window 512 located substantially centrally along the bottom surface 116. Dimensions of the window 512 may be substantially similar to dimensions of the windows 112. It is noted, however, that the window 512 may assume any dimensions without deviating from the scope of the invention. Furthermore, although the window 512 is depicted with a substantially rectangular shape, any other shape may be used without deviating from the scope of the invention. In an operative configuration, the box 502 may be provided with the foam inlays 450, 452 of FIG. 13, as described in greater detail earlier. As those skilled in the art will understand, the window 512 may aid in visualization of the medical device 10 when seated within the foam inlays 450, 452 and positioned within a cavity of the box 502 in an operative configuration. It is further noted that, in an alternate embodiment, the window 512 may be omitted from the box 502.

In yet another embodiment, the removable labels 532 may be positioned over the sealing arrangement 130 of the box 102. The removable labels 532 of this embodiment may extend from the tab 132 to a portion of the bottom surface 116. Grasping and pulling the labels causes the tab 132 to be pulled away and separated from the box 102.

It is noted that the exemplary boxes 102, 202, 302, 502 disclosed above may be used in combination with either of the inlays 140, 240, 340, 440 without deviating from the scope of the invention. Furthermore, it will be apparent to those skilled in the art that various other modifications and variations can be made in the structure and the methodology of the present invention, without departing from the spirit or scope of the invention. For example, the window 512 and the removable labels 532 may be provided on any of the boxes 102, 202, 302, 502. Thus, it is intended that the present invention cover the modifications and variations of this invention provided that they come within the spirit of the appended claims and their equivalents.

What is claimed is:

1. A housing for a medical device, comprising:
a container having an interior space sized and shaped to house a medical device sealed within a packet, the container having a first window configured to provide visual access of the medical device, the container defining a cavity therewithin; and
an insert configured for insertion into the container, outer dimensions of the insert conforming to inner dimensions of the container to prevent movement of the insert within the container, the insert being configured to frictionally retain the medical device therewithin, wherein the insert includes first and second walls having first and second openings extending therethrough, respectively, wherein the first and second walls are substantially the same shape and size and are individually insertable into the cavity of the container, wherein the first and second openings are positioned so that, when inserted into the container in a desired alignment, the first and second openings coincide with the first window so that the medical device retained therein is visible, and wherein the first wall is integrally formed with a body of a container and is foldable into the cavity of the container.

2. The housing of claim 1, wherein the first and second walls are connected to one another, the first and second walls being movable between an open configuration in which the first and second walls are separated from one another and a closed configuration in which the first and second walls are folded to contact one another along a length thereof such that the first and second openings are aligned with one another to define a medical device receiving cavity configured to house the medical device, wherein, in the closed configuration, the first and second walls apply a frictional clamping force to the packet to prevent movement of the medical device relative to the insert.

3. The housing of claim 1, wherein the first and second walls are removable from the cavity.

4. The housing of claim 1, wherein the first wall is formed of one of foam and cardboard and wherein the second wall is formed of one of foam and cardboard.

5. The housing of claim 1, wherein the container is a box having a rectangular shape.

6. The housing of claim 1, wherein the container comprises a first opening arrangement including a first tab open to a perforated portion and configured such that pulling the first tab in a direction away from the container tears the perforated portion to permit a first top surface to be folded away from the container and permit access to the interior space.

7. The housing of claim 6, wherein the container comprises a second opening arrangement including a second tab open to a perforated portion and configured such that pulling the second tab in a direction away from the container tears the perforated portion to permit the first surface to be folded away from the container and permit access to the interior space.

8. The housing of claim 7, wherein the container comprises a second window on the first surface, the second tab extending over a portion of the second window.

9. The housing of claim 8, wherein the first and second windows are covered by a transparent film.

10. The housing of claim 8, further comprising a third window provided on a second bottom surface of the housing, the second surface being located opposite the first surface in an assembled configuration.

11. The housing of claim 1, wherein a first tab extends over a portion of the first window.

12. The housing of claim 1, wherein the container is one of top-loading and side-loading.

13. The housing of claim 1, wherein the container comprises a sealing arrangement including an adhesive portion maintaining the container in a closed configuration, the sealing arrangement including a non-adhesive tab extending from the adhesive portion, the tab being configured such that pulling the tab away from the container separates the adhesive portion from the container permitting access to the interior space.

14. The housing of claim 13, wherein the adhesive portion may be reattached to the container to re-seal the container.

15. A housing for a medical device, comprising:

a container having an interior space sized and shaped to house a medical device sealed within a packet, the container having a first window configured to provide visual access of the medical device, the container defining a cavity therewithin; and an insert configured for insertion into the container, outer dimensions of the insert conforming to inner dimensions of the container to prevent movement of the insert within the container, the insert being configured to frictionally retain the medical device therewithin, wherein the insert includes first and second walls having first and second openings extending therethrough, respectively, wherein the first and second walls are substantially the same shape and size and are individually insertable into the cavity of the container, wherein the first and second openings are positioned so that, when inserted into the container in a desired alignment, the first and second openings coincide with the first window so that the medical device retained therein is visible, and wherein only the second wall is removable from the cavity.

16. The housing of claim 15, wherein the first and second walls are connected to one another, the first and second walls being movable between an open configuration in which the first and second walls are separated from one another and a closed configuration in which the first and second walls are folded to contact one another along a length thereof such that the first and second openings are aligned with one another to define a medical device receiving cavity configured to house the medical device, wherein, in the closed configuration, the first and second walls apply a frictional clamping force to the packet to prevent movement of the medical device relative to the insert.

17. The housing of claim 15, wherein the first and second walls are removable from the cavity.

18. The housing of claim 15, wherein the first wall is formed of one of foam and cardboard and wherein the second wall is formed of one of foam and cardboard.

19. The housing of claim 15, wherein the container is a box having a rectangular shape.

20. The housing of claim 15, wherein the container comprises a first opening arrangement including a first tab open to a perforated portion and configured such that pulling the first tab in a direction away from the container tears the perforated portion to permit a first top surface to be folded away from the container and permit access to the interior space.

* * * * *